United States Patent
Willard (10) Patent No.: US 10,932,905 B2
(45) Date of Patent: Mar. 2, 2021

(54) INTRODUCER SHEATH HAVING EXPANDABLE PORTIONS

(71) Applicant: St. Jude Medical, Cardiology Division, Inc., St. Paul, MN (US)

(72) Inventor: Steven N. Willard, Bloomington, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 224 days.

(21) Appl. No.: 15/971,097

(22) Filed: May 4, 2018

(65) Prior Publication Data

US 2018/0318078 A1 Nov. 8, 2018

Related U.S. Application Data (60) Provisional application No. 62/501,835, filed on May 5, 2017.

(51) Int. Cl.
*A61F 2/24* (2006.01)
*A61M 25/00* (2006.01)
(Continued)

(52) U.S. Cl.
CPC .......... *A61F 2/2436* (2013.01); *A61F 2/2427* (2013.01); *A61F 2/95* (2013.01); *A61M 25/0023* (2013.01); *A61M 25/0662* (2013.01); *A61M 2025/0024* (2013.01); *A61M 2025/0025* (2013.01)

(58) Field of Classification Search
CPC .. A61F 2/95; A61F 2/962; A61F 2/966; A61F 2/2436; A61F 2/2427; A61M 25/0023; A61M 25/0662; A61M 2025/0024; A61M 2025/0025
See application file for complete search history.

(56) References Cited

U.S. PATENT DOCUMENTS

| 3,657,744 A | 4/1972 | Ersek |
| 4,423,730 A | 1/1984 | Gabbay |

(Continued)

FOREIGN PATENT DOCUMENTS

| DE | 102005003632 A1 | 8/2006 |
| EP | 1129744 A1 | 9/2001 |

(Continued)

OTHER PUBLICATIONS

International Search Report for Application No. PCT/US2016/049888 dated Dec. 12, 2016.

(Continued)

*Primary Examiner* — Ashley L Fishback
(74) *Attorney, Agent, or Firm* — Lerner, David, Littenberg, Krumholz & Mentlik, LLP (57) ABSTRACT

An introducer sheath includes a body having a lumen extending between a leading end and a trailing end and having a collapsed condition with a first lateral cross-section, the first lateral cross-section being flower-shaped, the body being configured to transition from the collapsed condition to an expanded condition with a second lateral cross-section when an apparatus is passed through the lumen, the second lateral cross-section having a maximum dimension larger than a maximum dimension of the first lateral cross-section.

17 Claims, 8 Drawing Sheets

(51) Int. Cl.
 *A61M 25/06* (2006.01)
 *A61F 2/95* (2013.01)

(56) References Cited

U.S. PATENT DOCUMENTS

| | | | |
|---|---|---|---|
| 5,078,720 | A | 1/1992 | Burton et al. |
| 5,415,664 | A | 5/1995 | Pinchuk |
| 5,484,444 | A | 1/1996 | Braunschweiler et al. |
| 5,702,418 | A | 12/1997 | Ravenscroft |
| 5,824,041 | A | 10/1998 | Lenker et al. |
| 5,843,167 | A | 12/1998 | Dwyer et al. |
| 5,924,424 | A | 7/1999 | Stevens et al. |
| 5,968,068 | A | 10/1999 | Dehdashtian et al. |
| 5,980,533 | A | 11/1999 | Holman |
| 6,077,297 | A | 6/2000 | Robinson et al. |
| 6,190,357 | B1 * | 2/2001 | Ferrari ............... A61B 17/3439 604/102.01 |
| 6,269,819 | B1 | 8/2001 | Oz et al. |
| 6,306,141 | B1 | 10/2001 | Jervis |
| 6,391,050 | B1 | 5/2002 | Broome |
| 6,468,299 | B2 | 10/2002 | Stack et al. |
| 6,623,518 | B2 | 9/2003 | Thompson et al. |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,311,730 | B2 | 12/2007 | Gabbay |
| 7,510,572 | B2 | 3/2009 | Gabbay |
| 7,682,390 | B2 | 3/2010 | Seguin |
| 7,803,185 | B2 | 9/2010 | Gabbay |
| 8,840,663 | B2 | 9/2014 | Salahieh et al. |
| 2003/0050694 | A1 | 3/2003 | Yang et al. |
| 2004/0210304 | A1 | 10/2004 | Seguin et al. |
| 2005/0137695 | A1 | 6/2005 | Salahieh et al. |
| 2005/0137697 | A1 | 6/2005 | Salahieh et al. |
| 2005/0240200 | A1 | 10/2005 | Bergheim |
| 2006/0074484 | A1 | 4/2006 | Huber |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0055358 | A1 | 3/2007 | Krolik et al. |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2008/0004571 | A1 | 1/2008 | Voss |
| 2008/0071369 | A1 | 3/2008 | Tuval et al. |
| 2008/0147182 | A1 | 6/2008 | Righini et al. |
| 2009/0054975 | A1 | 2/2009 | del Nido et al. |
| 2009/0210052 | A1 * | 8/2009 | Forster ............... A61F 2/2418 623/2.38 |
| 2010/0004740 | A1 | 1/2010 | Seguin et al. |
| 2010/0286768 | A1 | 11/2010 | Alkhatib |
| 2010/0298931 | A1 | 11/2010 | Quadri et al. |
| 2011/0114700 | A1 | 5/2011 | Baxter, III et al. |
| 2011/0224678 | A1 | 9/2011 | Gabbay |
| 2011/0257734 | A1 | 10/2011 | Chalekian |
| 2011/0282287 | A1 | 11/2011 | Chalekian |
| 2013/0211324 | A1 | 8/2013 | Voss et al. |
| 2013/0297007 | A1 * | 11/2013 | Kuchela ............... A61F 2/97 623/1.23 |
| 2016/0296332 | A1 | 10/2016 | Zhou et al. |
| 2017/0014157 | A1 | 1/2017 | Coyle et al. |
| 2017/0021130 | A1 * | 1/2017 | Dye ............... A61M 25/04 |
| 2017/0049991 | A1 * | 2/2017 | Avneri ............... A61M 25/0023 |
| 2018/0104449 | A1 * | 4/2018 | Arnar ............... A61B 17/32053 |

FOREIGN PATENT DOCUMENTS

| | | |
|---|---|---|
| EP | 1157673 A2 | 11/2001 |
| EP | 1759645 A1 | 3/2007 |
| EP | 1926455 A2 | 6/2008 |
| WO | 02067782 A2 | 9/2002 |
| WO | 07071436 A2 | 6/2007 |
| WO | 08070797 A2 | 6/2008 |
| WO | 2009097650 A1 | 8/2009 |
| WO | 10051025 A1 | 5/2010 |
| WO | 2010081105 A1 | 7/2010 |
| WO | 10087975 A1 | 8/2010 |
| WO | 2014124283 A1 | 8/2014 |
| WO | 2016144115 A1 | 9/2016 |
| WO | 2017040774 A1 | 3/2017 |

OTHER PUBLICATIONS

Ruiz, Carlos, Overview of PRE-CE Mark Transcatheter Aortic Valve Technologies, Euro PCR dated May 25, 2010.

Percutaneous aortic valve replacement: resection before implantation, 836-840, Quaden, Rene et al., European J. of Cardio-thoracic Surgery, 27 (2005).

International Search Report including Written Opinion for Application No. PCT/US2018/031011 dated Jul. 31, 2018.

* cited by examiner

(PRIOR ART)

INTRODUCER SHEATH HAVING EXPANDABLE PORTIONS

CROSS REFERENCE TO RELATED APPLICATION

The present application claims the benefit of the filing date of U.S. Provisional Patent Application No. 62/501,835 filed May 5, 2017, the disclosure of which is hereby incorporated herein by reference.

BACKGROUND OF THE INVENTION

The present invention is related to percutaneous medical procedures, and more particularly to devices providing access into the body for performing percutaneous medical procedures. Still more particularly, the present invention is related to prosthetic heart valve replacement, including devices, systems, and methods for transcatheter delivery of collapsible prosthetic heart valves into a patient.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Despite the various improvements that have been made to the collapsible prosthetic heart valve delivery process, conventional delivery devices, systems, and methods suffer from some shortcomings. For example, in conventional delivery devices for self-expanding valves, large introducers risk traumatizing the iliac or femoral arteries, and the risk of trauma increases with introducers having larger diameters.

There therefore is a need for further improvements to the devices, systems, and methods for transcatheter delivery of collapsible prosthetic heart valves, and in particular, the introduction of such prosthetic heart valves into the heart. Among other advantages, the present invention may address one or more of these needs.

BRIEF SUMMARY OF THE INVENTION

In some embodiments, an introducer sheath includes a body having a lumen extending between a leading end and a trailing end and having a collapsed condition with a first lateral cross-section, the first lateral cross-section being flower-shaped, the body being configured to transition from the collapsed condition to an expanded condition with a second lateral cross-section when an apparatus is passed through the lumen, the second lateral cross-section having a maximum dimension larger than a maximum dimension of the first lateral cross-section.

In some embodiments, a method of delivering a medical apparatus into a patient includes piercing an opening in the patient's body at an insertion location, at least partially inserting an introducer sheath into the opening, the introducer sheath including a body having a lumen extending between a leading end and a trailing end and having a collapsed condition with a first lateral cross-section, the first lateral cross-section being flower-shaped, the body being configured to transition from the collapsed condition to an expanded condition with a second lateral cross-section when a medical apparatus is passed through the lumen, the second lateral cross-section having a maximum dimension larger than a maximum dimension of the first lateral cross-section, inserting the medical apparatus through the lumen of the body, wherein the medical apparatus transitions the body from the collapsed condition to the expanded condition, and removing the medical apparatus from the lumen of the body, whereby the body returns from the expanded condition to the collapsed condition.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the terms "proximal," "distal," "leading" and "trailing" are to be taken as relative to a user using the disclosed delivery devices. "Proximal" or "trailing end" are to be understood as relatively close to the user, and "distal" or "leading end" are to be understood as relatively farther away from the user. Also, as used herein, the words "substantially," "approximately," "generally" and "about" are intended to mean that slight variations from absolute are included within the scope of the structure or process recited.

Figure 1A:
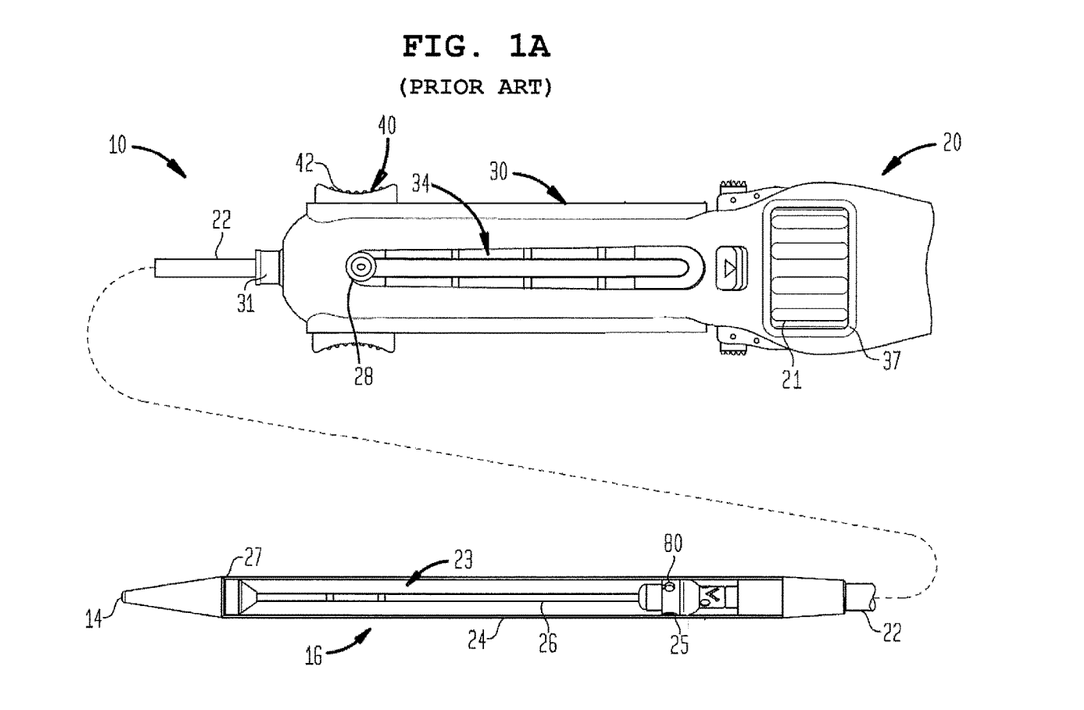
FIG. 1A is a top plan view of a portion of an operating handle of a prior art delivery device for a collapsible prosthetic heart valve, shown with a partial longitudinal cross-section of the distal portion of a catheter assembly.
Figure 1B:
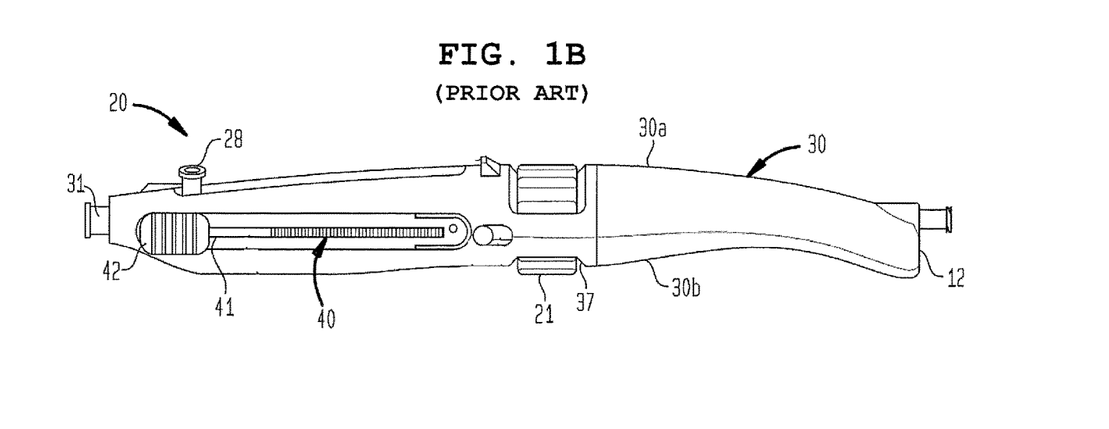
FIG. 1B is a side elevational view of the handle of FIG. 1A.

In the description which follows, the structure and function of a transaortic or transfemoral delivery device will be described. It will be understood, however, that the devices and methods disclosed herein also may be used with a transapical or transseptal delivery device. Indeed, the devices and methods described herein may be used in connection with any minimally invasive procedure to provide a passageway for any type of small profile medical device or instrument into a patient's body. An exemplary transaortic delivery device 10 for delivering a prosthetic heart valve into a patient is shown in FIGS. 1A and 1B. Transaortic delivery device 10 has a catheter assembly 16 for delivering the heart valve to and deploying the heart valve at a target location, and an operating handle 20 for controlling deployment of the valve from the catheter assembly. Delivery device 10 extends from a proximal end 12 to an atraumatic tip 14 at the distal end of catheter assembly 16. Catheter assembly 16 is adapted to receive a collapsible prosthetic heart valve (not shown) in a compartment 23 defined around an inner shaft 26 and covered by a distal sheath 24.

Inner shaft 26 may extend from operating handle 20 to atraumatic tip 14 of the delivery device, and may include a retainer 25 affixed thereto at a spaced distance from tip 14 and adapted to hold a collapsible prosthetic valve in compartment 23. Retainer 25 may have recesses 80 therein that are adapted to hold corresponding retention members of the valve. Inner shaft 26 may be made of a flexible material such as braided polyimide or polyetheretherketone (PEEK), for example. Using a material such as PEEK may improve the resistance of inner shaft 26 to kinking while catheter assembly 16 is tracking through the vasculature of a patient.

Distal sheath 24 surrounds inner shaft 26 and is slidable relative to the inner shaft such that it can selectively cover or uncover compartment 23. Distal sheath 24 is affixed at its proximal end to an outer shaft 22, the proximal end of which is connected to operating handle 20 in a manner to be described. Distal end 27 of distal sheath 24 abuts atraumatic tip 14 when the distal sheath is fully covering compartment 23, and is spaced apart from the atraumatic tip when compartment 23 is at least partially uncovered.

Operating handle 20 is adapted to control deployment of a prosthetic valve located in compartment 23 by permitting a user to selectively slide outer shaft 22 proximally or distally relative to inner shaft 26, thereby respectively uncovering or covering the compartment with distal sheath 24. Outer shaft 22 may be made of a flexible material such as nylon 11 or nylon 12, and it may have a round braid construction (i.e., round cross-section fibers braided together) or flat braid construction (i.e., rectangular cross-section fibers braided together), for example.

The proximal end of inner shaft 26 may be connected in a substantially fixed relationship to an outer housing 30 of operating handle 20, and the proximal end of the outer shaft 22 may be affixed to a carriage assembly 40 that is slidable along a longitudinal axis of the handle housing, such that a user can selectively slide the outer shaft relative to the inner shaft by sliding the carriage assembly relative to the housing. Operating handle 20 may further include a hemostasis valve 28 having an internal gasket adapted to create a seal between inner shaft 26 and the proximal end of outer shaft 22.

As shown, handle housing 30 includes a top portion 30a and a bottom portion 30b. Top and bottom portions 30a and 30b may be individual components joined to one another as shown in FIG. 1B. Collectively, top and bottom portions 30a and 30b define an elongated space 34 in housing 30 in which carriage assembly 40 may travel. Optionally, top and bottom portions 30a and 30b may further form a substantially cylindrical boss 31 for accepting a clip, as will be described below. Elongated space 34 preferably permits carriage assembly 40 to travel a distance that is at least as long as the anticipated length of the prosthetic valve to be delivered (e.g., at least about 50 mm), such that distal sheath 24 can be fully retracted from around the prosthetic valve. Carriage assembly 40 includes a pair of carriage grips 42, each attached to a body portion 41. Although the carriage assembly 40 is shown in FIGS. 1A and 1B as having two carriage grips 42, that need not be the case.

Handle housing 30 further defines a pocket 37 that extends through top portion 30a and bottom portion 30b for receiving a deployment actuator 21. Pocket 37 is sized and shaped to receive deployment actuator 21 with minimal clearance, such that the location of deployment actuator remains substantially fixed relative to housing 30 as it is rotated. Deployment actuator 21 may be internally coupled to body portion 41 via a threaded shaft or other suitable connection such that rotation of the deployment actuator in one direction (either clockwise or counterclockwise) pulls the body portion 41 of carriage assembly 40 proximally through elongated space 34.

To use operating handle 20 to deploy a prosthetic valve that has been loaded into compartment 23 and covered by distal sheath 24, the user may rotate deployment actuator 21, causing carriage assembly 40 to slide proximally within elongated space 34 in housing 30. Because distal sheath 24 is affixed to outer shaft 22, which in turn is affixed to carriage assembly 40, and because inner shaft 26 is fixed to housing 30, sliding the carriage assembly proximally relative to the housing will retract the distal sheath proximally from compartment 23, thereby exposing and initiating deployment of the valve located therein.

Figure 2:
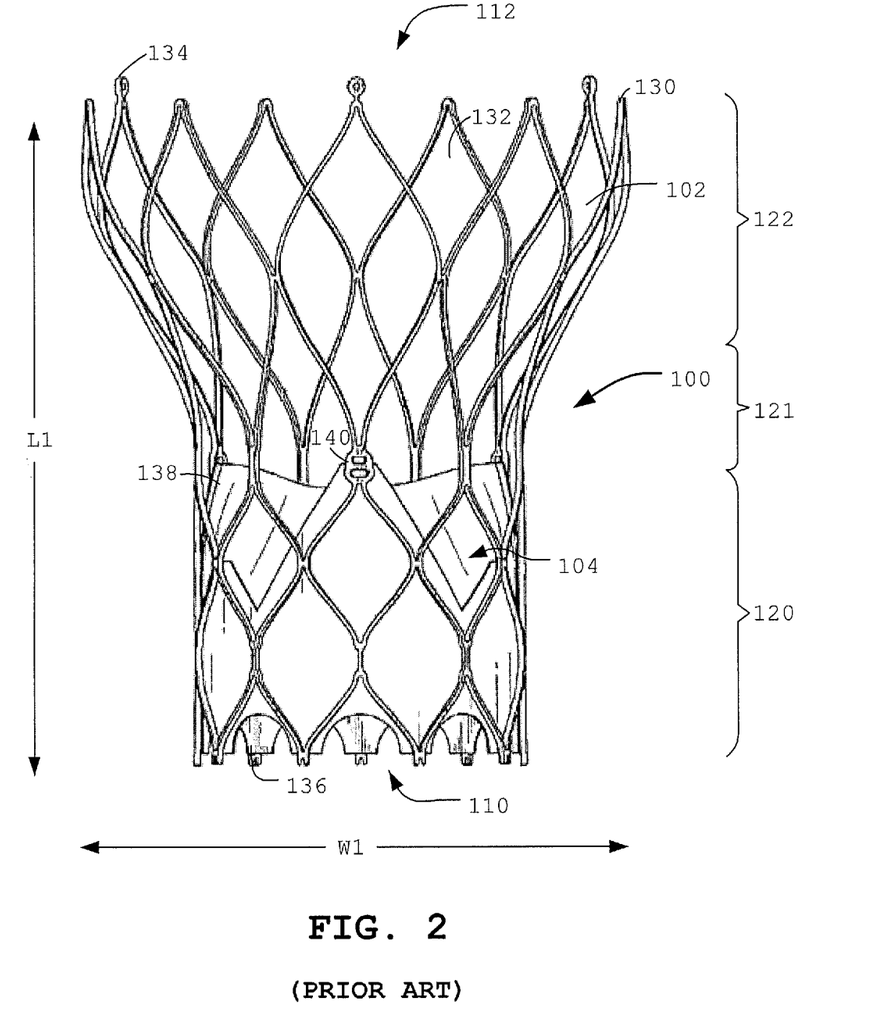
FIG. 2 is a side elevational view of a prior art prosthetic heart valve.

Delivery device 10 may be used to implant a medical device such as a collapsible stent-supported prosthetic heart valve 100 having a stent 102 and a valve assembly 104 (FIG. 2). Prosthetic heart valve 100 is designed to replace a native tricuspid valve of a patient, such as a native aortic valve. It should be noted that while the devices disclosed herein are described predominantly in connection with their use to implant a prosthetic aortic valve and a stent having a shape as illustrated in FIG. 2, the valve could be a bicuspid or other valve, such as the mitral valve.

The expandable stent 102 of prosthetic heart valve 100 may be formed from biocompatible materials that are capable of self-expansion, such as, for example, shape memory alloys, such as the nickel-titanium alloy known as "nitinol," or other suitable metals or polymers. Stent 102 extends in a length direction L1 from proximal or annulus end 110 to distal or aortic end 112, and includes annulus section 120 adjacent proximal end 110, transition section 121, and aortic section 122 adjacent distal end 112. Annulus section 120 has a relatively small cross-section in the expanded condition, while aortic section 122 has a relatively large cross-section in the expanded condition. Preferably, annulus section 120 is in the form of a cylinder having a substantially constant diameter along its length. Transition section 121 may taper outwardly from annulus section 120 to aortic section 122. Stent 102 may also have different shapes, such as a flared or conical annulus section, a less-bulbous aortic section, and the like, and a differently shaped transition section 121. Each of the sections of stent 102 includes a plurality of struts 130 forming cells 132 connected to one another in one or more annular rows around the stent. For example, as shown in FIG. 2, annulus section 120 may have two annular rows of complete cells 132 and aortic section 122 and transition section 121 may each have one or more annular rows of partial cells 132. Cells 132 in aortic section 122 may be larger than cells 132 in annulus section 120 to better enable prosthetic valve 100 to be positioned in the native valve annulus without the stent structure interfering with blood flow to the coronary arteries. Each of cells 132 has a length in length direction L1 of the stent and a width in a perpendicular direction W1.

Stent 102 may include one or more retaining elements 134 at distal end 112 thereof, retaining elements 134 being sized and shaped to cooperate with recesses 80 in retainer 25 of delivery device 10. The engagement of retaining elements 134 with portions of delivery device 10 helps maintain prosthetic heart valve 100 in assembled relationship with the delivery device, minimizes longitudinal movement of the prosthetic heart valve relative to the delivery device during unsheathing or resheathing procedures, and helps prevent rotation of the prosthetic heart valve relative to the delivery device as the delivery device is advanced to the target location and the heart valve deployed.

Valve assembly 104 of prosthetic heart valve 100 preferably is positioned in annulus section 120 of stent 102 and secured to the stent. Valve assembly 104 includes cuff 136 and a plurality of leaflets 138 which collectively function as a one-way valve by coapting with one another. As a prosthetic aortic valve, valve 100 has three leaflets 138.

Although cuff 136 is shown in FIG. 2 as being disposed on the luminal or inner surface of annulus section 120, it is contemplated that cuff 136 may be disposed on the abluminal or outer surface of annulus section 120 or may cover all or part of either or both of the luminal and abluminal surfaces. Both cuff 136 and leaflets 138 may be wholly or partly formed of any suitable biological material or polymer such as, for example, polytetrafluoroethylene (PTFE).

Leaflets 138 may be attached along their belly portions to cuff 136 or to stent 102, with the commissure between adjacent leaflets 138 being attached to a commissure feature 140. As can be seen in FIG. 2, each commissure feature 140 may lie at the intersection of four cells 132, two of the cells being adjacent one another in the same annular row, and the other two cells being in different annular rows and lying in end-to-end relationship. Preferably, commissure features 140 are positioned entirely within annulus section 120 or at the juncture of annulus section 120 and transition section 121. Commissure features 140 may include one or more eyelets which facilitate the suturing of the leaflet commissure to stent 102.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device, including delivery device 10 described above. During delivery, prosthetic heart valve 100 is disposed inside compartment 23 of delivery device 10 in the collapsed condition. The delivery device may be introduced into a patient using a transfemoral, transapical, transseptal or any other percutaneous approach. Once the delivery device has reached the target site, the user may deploy prosthetic heart valve 100 in the manner described above. Upon deployment, prosthetic heart valve 100 expands so that annulus section 120 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

An introducer sheath may be useful to advance the delivery device to a target location. Specifically, an incision may be formed in the patient's body and the introducer sheath may be placed through the incision to provide a passageway for advancing a medical device into the patient's body. It has been found that larger introducers risk traumatizing body tissue and that the risk of trauma increases with time. Thus, it is desirable to have a small introducer sheath that locally expands as necessary to allow the passage of medical instruments and then contracts when nothing is disposed therein. Although introducer sheaths are described below in connection with the delivery of a prosthetic heart valve into a patient, it will be understood that the concepts described may be useful for any interventional procedure in which an apparatus, such as a medical device or instrument, is passed through an introducer sheath for delivery, implantation or surgical procedures, such as other cardiac repair procedures, balloon angioplasty, laparoscopic surgical procedures, peripheral interventional procedures, and the like.

Figures 3A, 3B:
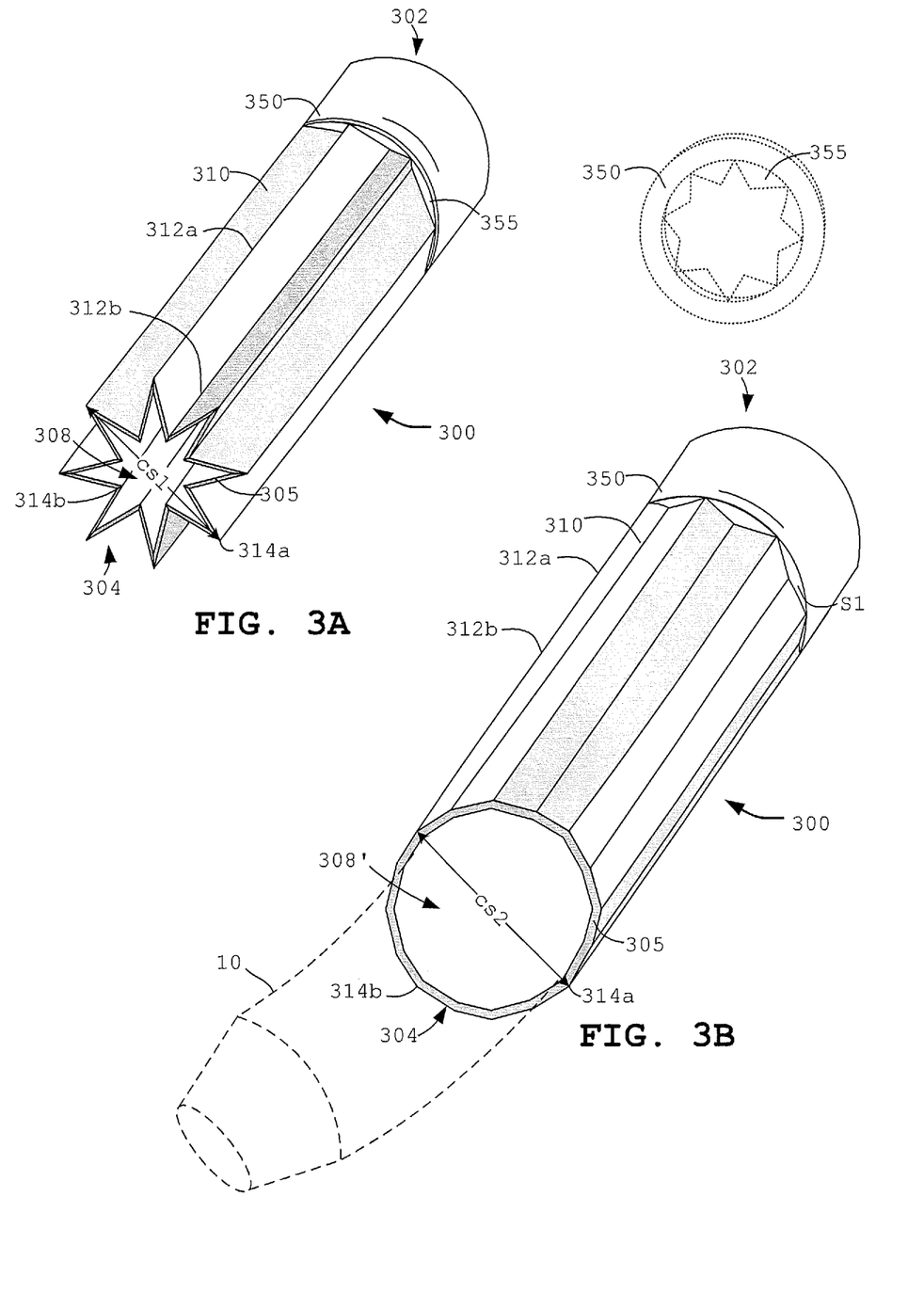
FIGS. 3A and 3B are perspective views of one embodiment of an expandable introducer in the collapsed and expanded conditions, respectively.

FIG. 3A illustrates an introducer sheath 300 in a collapsed condition. Introducer sheath 300 extends between trailing end 302 and leading end 304 and includes body 305 that is longitudinally pleated so as to include a plurality of generally rectangular segments 310 extending from trailing end 302 to leading end 304, segments 310 being connected to one another in a circumferential manner to define lumen 308 through body 305. Body 305 has a substantially star-shaped cross-section in the collapsed condition, with each segment 310 being joined to adjacent segments along edges 312a, 312b to define outer vertices 314a and inner vertices 314b of the star-shaped body. As shown, body 305 includes eight outer vertices 314a and eight inner vertices 314b, but it will be understood that body 305 may include multiple segments 310 and that the term "star-shaped configuration" may refer to any configuration having three or more outer vertices 314a and three or more inner vertices 314b. In its collapsed condition, introducer sheath 300 may have a maximum cross-section "cs1," measured from one outer vertex 314a to a diametrically opposed outer vertex 314a, that is between about 8 French and about 16 French, and preferably about 14 French.

Body 305 may be formed of a shape-memory material that is heat-set into the star-shaped configuration of FIG. 3A. In some examples, a thermoplastic elastomer, such as polyether block amide (PEBA) with a durometer reading of about 60 to about 70 on the Shore D scale, may be used to form body 305. Segments 310 may have a thickness of between about 0.001 inches and 0.01 inches and may preferably be about 0.006 inches, while edges 312a, 312b may have a reduced thickness of about 0.004 inches, such that vertices 314a, 314b are formed at predetermined positions to act as living hinges.

Body 305 may be flexible so that when a large instrument or medical device, such as delivery device 10, is passed through lumen 308, segments 310 are capable of being pushed radially outward so that body 305 transitions from the collapsed condition of FIG. 3A to a substantially tubular expanded condition shown in FIG. 3B. Once the large device or instrument has passed through the lumen, body 305 may contract once again to its heat-set star configuration.

It is preferable that introducer sheath 300 provide an adequate seal with the surrounding body tissue through which it passes. While a substantially circular cross-section (FIG. 3B) is capable of providing such a seal, the star-shaped cross-section to which body 305 will return after a device has been passed through lumen 308 may in some instances not provide an adequate seal. In at least some examples, a sealing ring 350 having elastomeric portions 355 may be disposed around body 305 adjacent trailing end 302, as shown in FIG. 3A, to provide adequate sealing at the trailing end 302 of introducer sheath 300. With ring 350 in place, elastomeric portions 355 fill valleys of the star-shaped configuration (e.g., elastomeric portions 355 have a substantially triangular cross-section defined by the inner circumference of ring 350 and two adjacent segments 310, extending along segments 310 to an inner vertex 314b). Elastomeric portions 355 may be substantially flexible such that as body 305 expands, the elastomeric portions collapse between body 305 and sealing ring 350, as shown in FIG. 3B. Sealing ring 350 may have a fixed circumference. In some examples, sealing ring 350 may be longer (e.g., approximately 3 inches) and forms a smooth transition to the body as shown. Thus, in all conditions, an adequate seal with body tissue is provided at trailing end 302, such as, for example, the femoral arterial wall. In one example, in its expanded condition, introducer sheath 300 may have an enlarged lumen 308, with a maximum outer cross-section "cs2" that is between about 18 French and about 20 French. In some examples, cs2 may be as large as 24 French.

In use, an incision may be made in the ascending aorta, left ventricle, or other target location and introducer sheath 300 may be advanced into the body at the target location in the collapsed condition of FIG. 3A and may remain in the collapsed condition until the user is ready to advance instruments or devices through lumen 308. Trailing end 302 may remain outside of the body. As large-diameter instruments are advanced through lumen 308 from trailing end 302 to leading end 304, segments 310 may be pushed radially outward to enlarge lumen 308 at certain local positions along the length of body 305 (e.g., not all of body 305 needs to be expanded, but only those portions of body 305 that are subject to a radially outward force from a medical device or instrument). A medical device or other instrument, such as delivery device 10, may be advanced and retracted through lumen 308 of introducer sheath 300 and the procedure may continue with introducer sheath 300 in place, the cross-section of the introducer sheath expanding as necessary when a medical device or other instruments push segments 310 outwardly, and then returning to the star-shaped configuration when no radially outward force is exerted thereon. While instruments are advanced, the cross-section of introducer sheath 100 may be changed to mimic the cross-section of the instruments. For example, if the instrument is wider than it is thick, introducer sheath 300 may expand to an oval, oblong or even substantially flat cross-section.

Ring 350 may serve to provide continuous sealing of introducer sheath 300 adjacent trailing end 302 with respect to the body tissue at all times as the introducer sheath expands and contracts. Specifically, sealing ring 350 may abut body tissue and surface 51 (i.e., the surface facing leading end 304) of sealing ring 350 may contact body tissue to provide an adequate seal around the circumference of introducer 300. Upon completion of the procedure, any medical devices and instruments may be removed from lumen 308 and the empty, collapsed introducer sheath may be withdrawn from the patient.

Figures 4A, 4B:
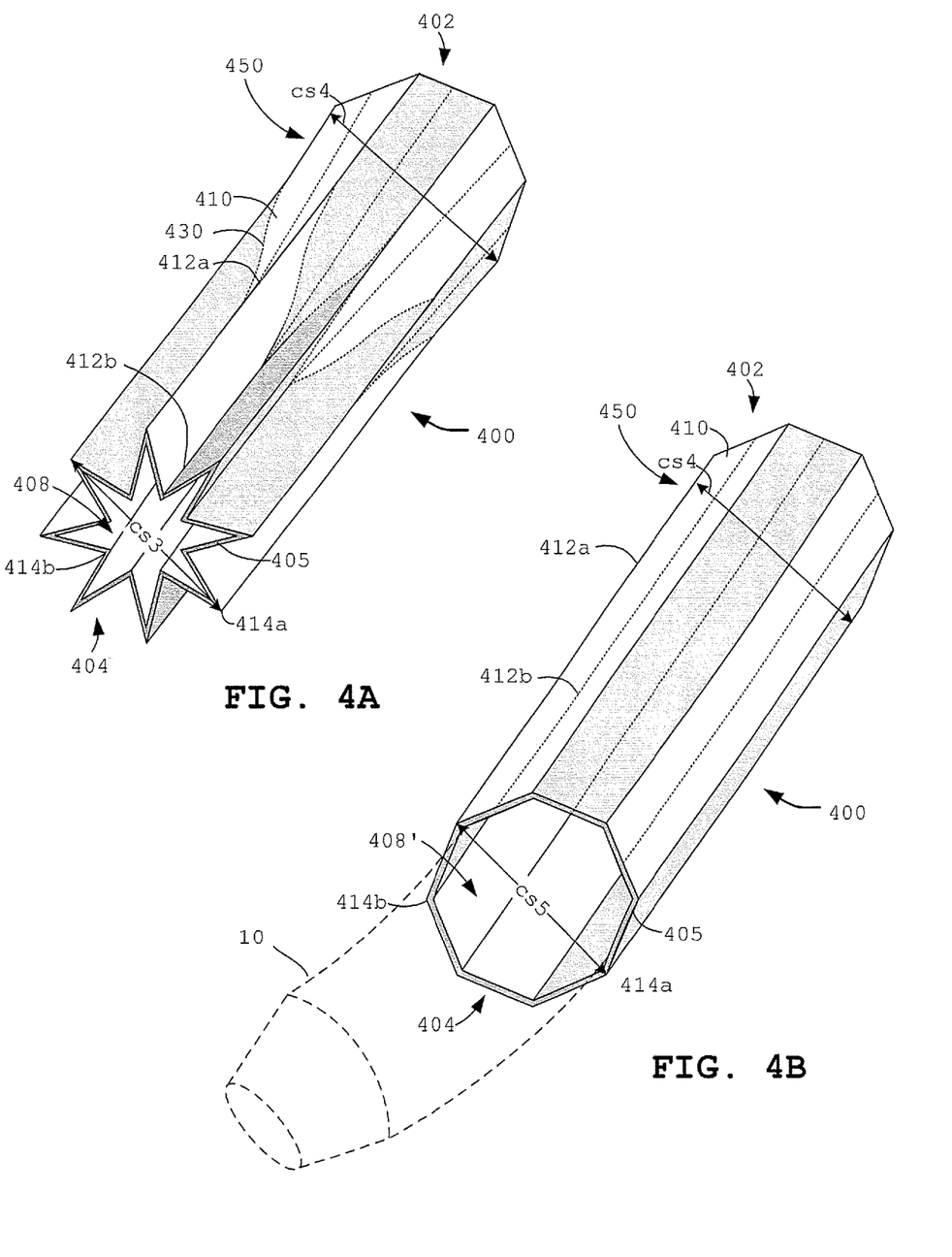
FIGS. 4A and 4B are perspective views of another embodiment of an expandable introducer in the collapsed and expanded conditions, respectively.

A second embodiment of an introducer sheath having expandable portions is shown in FIGS. 4A and 4B. Introducer sheath 400 extends between trailing end 402 and leading end 404 and includes body 405 that is longitudinally pleated so as to include a plurality of generally rectangular segments 410 extending from trailing end 402 to leading end 404, segments 410 being connected to one another in a circumferential manner to define lumen 408 through body 405. In this case, body 405 includes sixteen segments 410.

In the collapsed condition, body 405 has a substantially star-shaped cross-section with edges 412a,b and eight outer vertices 414a and eight inner vertices 414b at leading end 404 and an octagonal cross-section at trailing end 402. Leading end 404 may transition from the star-shaped configuration in the collapsed condition to the octagonal configuration of trailing end 402 in the expanded condition. At the same time, trailing end 402 is capable of maintaining its octagonal shape (or substantially circular shape in the case of a body 405 having a larger number of segments) in both the collapsed condition and the expanded condition to provide sealing with body tissue throughout a procedure. Each segment 410 smoothly and gradually changes at transitions 430 approximately halfway between leading end 404 and trailing end 402 from the star-shaped configuration to the octagonal configuration as shown. In some examples, it may be possible to make the vertices softer to facilitate expansion and collapsing at certain regions.

In its collapsed condition, introducer sheath 400 may have a maximum cross-section "cs3" at leading end 404, measured from one outer vertex 414a to a diametrically opposed outer vertex 414a, that is between about 8 French and about 16 French, and a maximum outer cross-section "cs4" at trailing end 404 that is between about 18 French and about 20 French. Because trailing end 402 remains outside of the body, collapsing to a smaller cross-section is not necessary at this end of introducer sheath 400.

Body 405 may transition from the collapsed condition (FIG. 4A) to the expanded condition (FIG. 4B) as a medical device or instrument, such as delivery system 10, is advanced through lumen 408, such that the star-shaped configuration at leading end 404 transforms into an octagonal configuration as shown, the leading end 404 expanding to a cross-section "cs5" that is greater than the cross-section "cs3" in the collapsed condition. Meanwhile, the cross-section at trailing end 402 may stay constant at cross-section "cs4" (e.g., the trailing end does not collapse or expand). In at least some examples, cross-section "cs5" may be approximately equal to cross-section "cs4" and may be between about 18 French and about 20 French. In such a configuration, the use of a sealing ring is not necessary as the trailing end provides adequate sealing against tissue at all times.

Figures 5A, 5B:
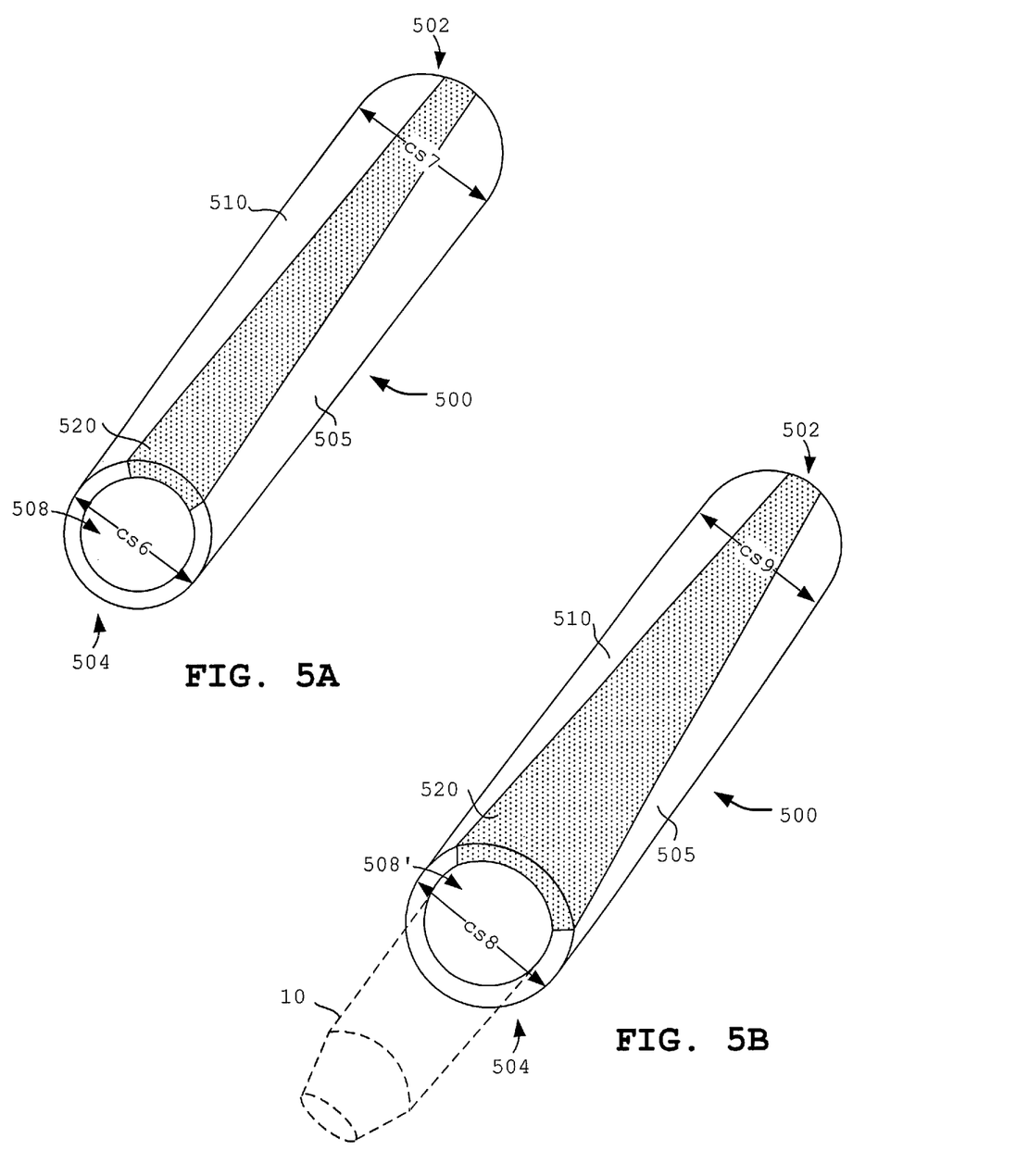
FIGS. 5A and 5B are perspective views of a further embodiment of an expandable introducer in the collapsed and expanded conditions, respectively.

In a third embodiment shown in FIGS. 5A and 5B, introducer sheath 500 extends between trailing end 502 and leading end 504 and includes a substantially cylindrical body 505 defining a lumen 508. Body 505 has a cross-section "cs6" at leading end 504 that is slightly smaller than the cross-section "cs7" at trailing end 502. For example, cross-section "cs6" may be between about 8 French and about 16 French, while cross-section "cs7" may be between about 18 French and about 20 French.

Body 505 may be formed of at least two portions, including a first portion 510 and a second portion 520. First portion 510 may include a first polymeric material, such as PEBAX® or other polymeric materials of a relatively high durometer reading, and second portion 520 may include a second polymeric material such as PEBAX® or other polymeric materials with a lower durometer reading than section 510. In at least some examples, second portion 520 is formed of a material that is more elastic than the material of first portion 510. As shown, first portion 510 forms the majority of body 505, while second portion 520 forms an elongated strip that extends from trailing end 502 to leading end 504, the strip gradually increasing in width from trailing end 502 to leading end 504. In one example, in the collapsed condition, second portion 520 forms approximately 5% of the circumference of body 505 at trailing end 502 and approximately 25% of the circumference of body 505 at leading end 504. In a variant of this embodiment, the second portion 520 may have a continuous width from trailing end 502 to leading end 504.

Due to the elasticity of second portion 520, sheath 500 may be capable of radial expansion to accommodate a medical device or instrument, such as delivery device 10, that travels through lumen 508. In the expanded condition, shown in FIG. 5B, outer cross-section "cs6" at leading end 504 has increased to outer cross-section "cs8" to allow delivery device 10 to pass through lumen 508. In some examples, cross-section "cs8" may be between about 18 French and about 20 French. As shown, elastic second portion 520 has stretched slightly to permit this change in cross-section. A change may also occur at trailing end 502 with cross-section "cs7" increasing to cross-section "cs9", although the change in cross-section at the trailing end may be less than the change in cross-section at leading end due to the larger initial cross-section at the trailing end. Further, in the illustrated embodiment, because second portion 520, which is more elastic than first portion 510, forms a greater circumferential percentage at leading end 504 than at trailing end 502, leading end 504 may be capable of greater expansion than trailing end 502.

Figure 6A:
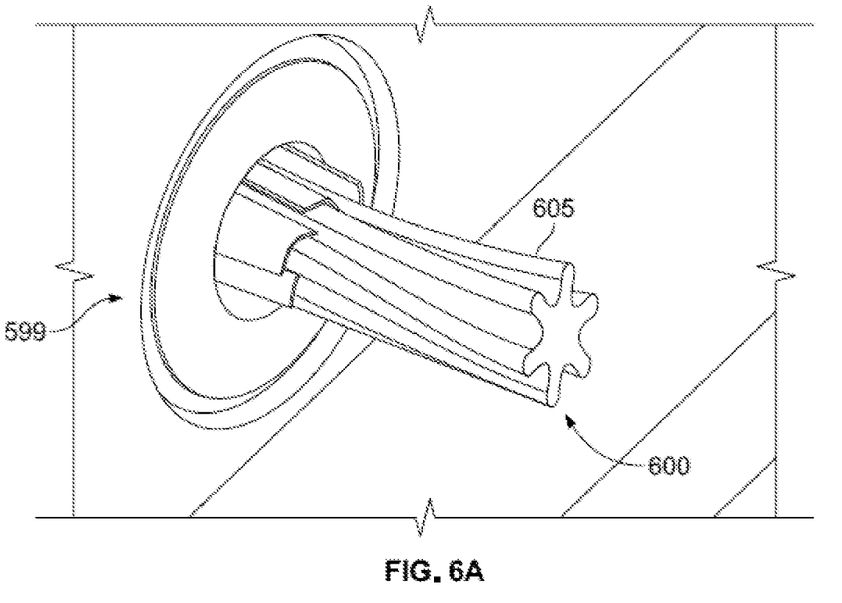
FIG. 6A is a perspective view of another embodiment of an expandable introducer exiting a die.
Figure 6B:
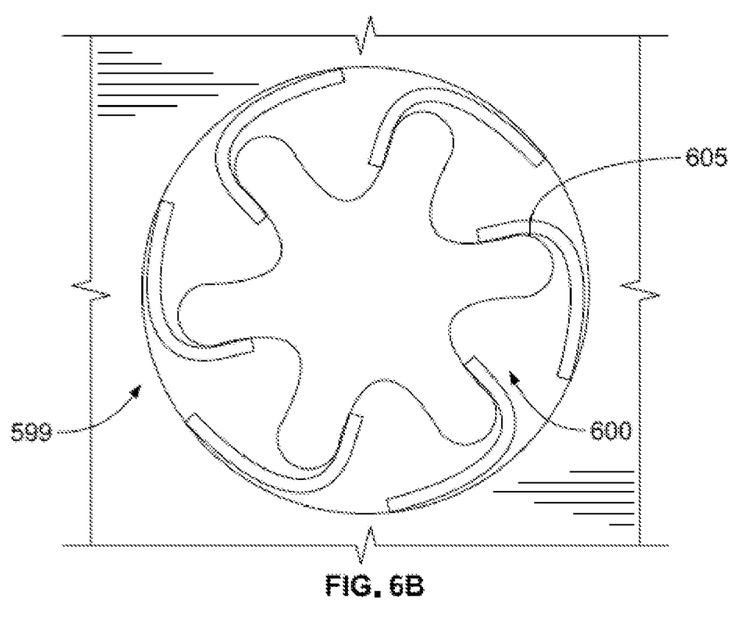
FIG. 6B is a perspective view of an end view of an expandable introducer similar to that of FIG. 6A disposed within the die.

Instead of an expandable introducer sheath having a star-shaped cross-sectional pattern as shown in FIG. 4A, a sheath having a flower-shaped lateral cross-section may be formed. FIG. 6A is a perspective view of one such expandable introducer sheath 600 exiting a heated die 599. Introducer sheath 600 is initially a substantially cylindrical tube before entering heated die 599. The shape of the die and heat from the die reform sheath 600 so that it has a flower-shaped lateral cross-section after it exits the heated die. For the PEBAX® polymer used to form sheath 600, die 599 is preferably heated to a temperature between about 165° C. and about 200° C., with a temperature of about 182° C. being particularly preferred. FIG. 6B is a perspective view of an end view of the expandable introducer sheath disposed within the die 599.

Figure 6C:
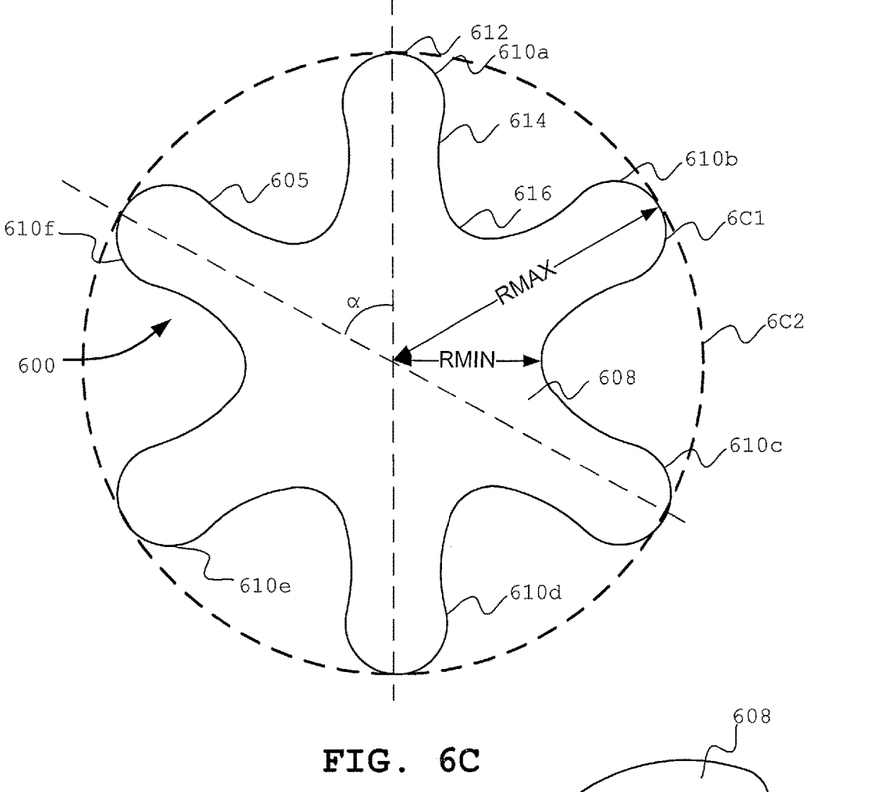
FIG. 6C is a schematic representation of an end view of an expandable introducer similar to that of FIG. 6A.

FIG. 6C is a more detailed schematic representation of a lateral cross-section of introducer sheath 600 having body 605 and lumen 608 in a first collapsed condition 6C1. Body 605 may be formed of any of the materials or combinations of materials described above, and may have a wall thickness of between about 0.001 inches and about 0.010 inches. In at least some examples, body 605 has a wall thickness of between about 0.003 inches and about 0.008 inches. As shown, introducer sheath 600 includes six lobes or petals 610a-610f. It will be understood that a different number of petals are possible, including two, three, four, five, seven, eight or nine or more petals. In the example shown, the petals are equally spaced around the circumference of introducer sheath 600, each petal being oriented at an angle α from an adjacent petal. For example, with six petals, as shown, each petal 610 may be spaced from an adjacent petal by approximately 60 degrees. Each petal 610 includes an enlarged head 612 and a narrowed or tailored neck region 614 that leads to a valley 616 between adjacent petals. In at least some examples, the maximum radius of petals 610 from the center of introducer sheath 600, shown as RMAX, is between about 0.20 inches and about 0.30 inches, and the radius of valleys 616 from the center of the introducer sheath, shown as RMIN, is between about 0.10 inches and about 0.20 inches.

Body 605 may be configured to include one or more portions having the flower-shaped lateral cross-section in the absence of external forces. That is, without applying any force to body 605, a portion of body 605 may have the flower-shaped lateral cross-section. A portion of body 605 may then transition from the collapsed condition 6C1 to the expanded condition 6C2 having a larger cross-section, shown in dashed lines in FIG. 6C, as a medical device or instrument, such as a delivery system, is advanced through lumen 608, such that the flower-shaped configuration transforms into a substantially circular expanded configuration as shown. It will be understood that while the expanded condition 6C2 is shown as being substantially circular, it is possible that a perfectly circular cross-section may not result, and that, depending on the size of the device being passed through the lumen, sheath 600 may keep a shape having one or more of the petals 610 in a collapsed or partially collapsed condition. For example, in FIG. 6D, a relatively small delivery device or tool 700 is inserted through sheath 600. The sheath 600 has expanded to accommodate tool 700, but two petals 610 remain in the collapsed condition.

Figure 6D:
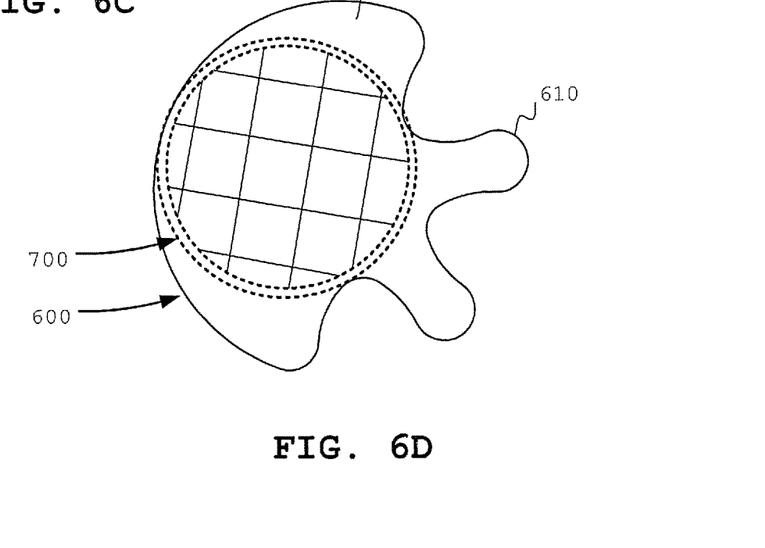
FIG. 6D is a schematic representation of an end view of an expandable introducer similar to that of FIG. 6A with a tool being inserted therethrough.

Additionally, it will be understood that the body 605 may transition as the delivery device or tool is inserted therethrough. Thus, at a given moment during insertion, body 605 may have a first expanded condition at a first location where the delivery device is located, and a second collapsed condition at a location distal to the delivery device. Additionally, portions of the body in the expanded condition may return to the collapsed condition once the delivery device has been removed (e.g., when no radially outward force is applied thereto).

Figure 7A:
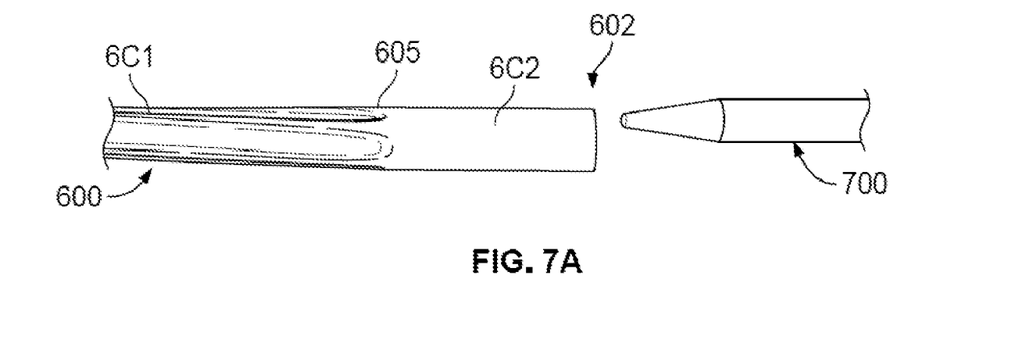
FIGS. 7A-C are side elevation views of a delivery device being advanced through an introducer sheath.
Figure 7B:
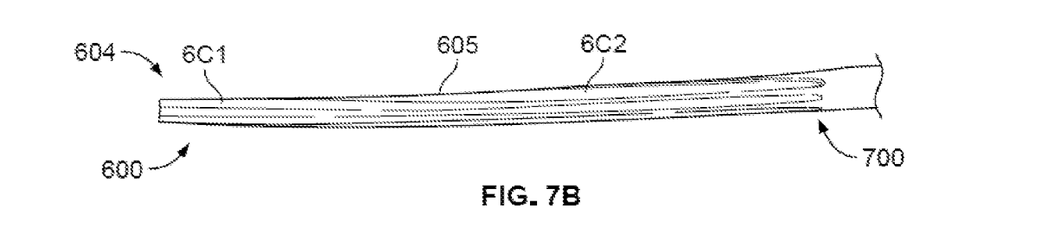
Figure 7C:
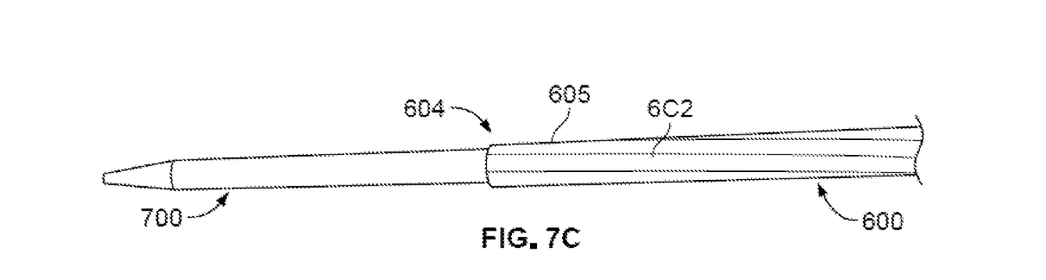

FIGS. 7A-C are side elevational views of a delivery device 700 for a prosthetic heart valve being advanced through an introducer sheath 600 from a trailing end 602 to a leading end 604 of the sheath. As shown, in an initial condition, trailing end 602 of sheath 600 has an expanded circular cross-section 6C2, while leading end 604 remains in a collapsed flower-shaped cross-section 6C1 (FIG. 7A). This configuration may be achieved by pushing only a desired portion of sheath 600 adjacent leading end 604 through the heated die, and not trailing end 602.

As delivery device 700 advances further through the lumen 608 of introducer sheath 600, more of body 605 transitions to the expanded condition (or an at least partially expanded condition) from the collapsed condition (i.e., from a flower-shaped cross-section to a substantially circular cross-section) (FIG. 7B). When delivery device 700 has been advanced distally past leading end 604, all of introducer sheath 600 is in a fully expanded, or at least partially expanded, condition (FIG. 7C).

Figure 8:
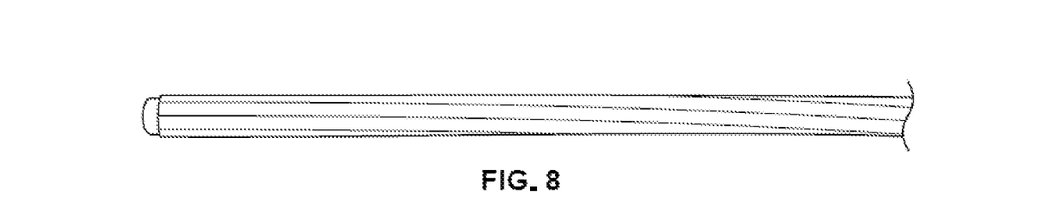
FIG. 8 is a side elevation view of another device being advanced through an introducer sheath.

FIG. 8 is a side elevational view of a delivery device 800 for another implantable medical device being advanced through introducer sheath 600. More particularly, delivery device 800 may be configured for the minimally invasive implantation of leadless cardiac pacemakers or other medical devices that may be implanted using minimally invasive techniques.

According to a first aspect of the disclosure, an introducer sheath includes:

a body having a lumen extending between a leading end and a trailing end and having a collapsed condition with a first lateral cross-section, the first lateral cross-section between flower-shaped, the body being configured to transition from the collapsed condition to an expanded condition with a second lateral cross-section when an apparatus is passed through the lumen, the second lateral cross-section having a maximum dimension larger than a maximum dimension of the first lateral cross-section; and/or the first lateral cross-section may include a plurality of petals; and/or the plurality of petals may be evenly spaced around a circumference of the body; and/or the first lateral cross-section may include six petals; and/or each of the petals may include an enlarged head portion and a tailored neck, adjacent ones of the plurality of petals being separated by a valley; and/or each of the valleys may have a radius from a center of the lumen of between about 0.10 inches and about 0.20 inches in the collapsed condition; and/or the body may be configured to transition to a maximum expanded condition, the body in the maximum expanded condition having a substantially circular cross-section; and/or the second lateral cross-section may have a size of between about 18 French and about 20 French; and/or the body in the collapsed condition may have one cross-sectional shape adjacent the leading end and another cross-sectional shape different from the one cross-sectional shape adjacent the trailing end; and/or the body in the expanded condition may have the one cross-sectional shape adjacent both the leading end and the trailing end; and/or the body may be configured to return to the collapsed condition in the absence of the apparatus in the lumen; and/or each of the plurality of petals may have a maximum radius from a center of the lumen of between about 0.20 inches and about 0.30 inches in the collapsed condition.

According to another aspect of the disclosure, a method of delivering a medical apparatus into a patient includes:

piercing an opening in the patient's body at an insertion location;

at least partially inserting an introducer sheath into the opening, the introducer sheath including a body having a lumen extending between a leading end and a trailing end and having a collapsed condition with the first lateral cross-section, the first lateral cross-section being flower-shaped, the body being configured to transition from the collapsed condition to an expanded condition with a second lateral cross-section when a medical apparatus is passed through the lumen, the second lateral cross-section having a maximum dimension larger than a maximum dimension of the first lateral cross-section;

inserting the medical apparatus through the lumen of the body, wherein the medical apparatus transitions the body from the collapsed condition to the expanded condition; and removing the medical apparatus from the lumen of the body, whereby the body returns from the expanded condition to the collapsed condition; and/or the method may include removing the medical apparatus through the lumen to allow the body to return to the collapsed condition; and/or the insertion location may be the ascending aorta; and/or the insertion location may be the left ventricle.

It will be understood that various modifications may be made to the disclosed embodiments without departing from the spirit of the disclosure. For example, an introducer sheath may be used to introduce a delivery device into the heart for prosthetic heart valve replacement, or may be used to introduce devices for valve repair at any of the heart valves (e.g., aortic valve, mitral valve, pulmonary valve, tricuspid valve). Additionally, an introducer sheath may be used to deliver instruments to repair other structures in the heart, such as the chordae tendineae, papillary muscles and the like. Introducer sheaths may also be used to deliver embolism prevention devices and stents, grafts and other cardiovascular devices into a patient, to introduce devices and instruments for other cardiac repair, to introduce any other medical instruments or devices into a patient's body in applications other than cardiovascular applications, and to access any bodily location where temporarily affixing a sheath within body tissue is useful.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A system comprising:
an introducer sheath having a body having a lumen extending between a leading end and a trailing end and having a collapsed condition with a first lateral cross-section, the first lateral cross-section being flower-shaped and including a plurality of rounded petals, the body being configured to transition from the collapsed condition to an expanded condition with a second lateral cross-section when an apparatus is passed through the lumen, the second lateral cross-section having a maximum dimension larger than a maximum dimension of the first lateral cross-section; and
an apparatus configured to pass through the lumen of the introducer sheath.

2. The system of claim 1, wherein the plurality of petals are evenly spaced around a circumference of the body.

3. The system of claim 1, wherein the first lateral cross-section includes six petals.

4. The system of claim 1, wherein each of the petals includes an enlarged head portion and a tailored neck, adjacent ones of the plurality of petals being separated by a valley.

5. The system of claim 4, wherein each of the valleys has a radius from a center of the lumen of between about 0.10 inches and about 0.20 inches in the collapsed condition.

6. The system of claim 1, wherein the body is configured to transition to a maximum expanded condition, the body in the maximum expanded condition having a substantially circular cross-section.

7. The system of claim 1, wherein the second lateral cross-section has a size of between about 18 French and about 20 French.

8. The system of claim 1, wherein the body in the collapsed condition has one cross-sectional shape adjacent the leading end and another cross-sectional shape different from the one cross-sectional shape adjacent the trailing end.

9. The system of claim 8, wherein the body in the expanded condition has the one cross-sectional shape adjacent both the leading end and the trailing end.

10. The system of claim 1, wherein the body is configured to return to the collapsed condition in the absence of the apparatus in the lumen.

11. The system of claim 1, wherein each of the plurality of petals has a maximum radius from a center of the lumen of between about 0.20 inches and 0.30 inches in the collapsed condition.

12. The system of claim 1, wherein each of the petals includes an enlarged head portion and a neck, adjacent ones of the plurality of petals being separated by a valley, a width of the valley being greater than a width of the enlarged head of the petal.

13. A method of delivering a medical apparatus into a patient, the method comprising:
   piercing an opening in the patient's body at an insertion location;
   at least partially inserting an introducer sheath into the opening, the introducer sheath including a body having a lumen extending between a leading end and a trailing end and having a collapsed condition with a first lateral cross-section, the first lateral cross-section being flower-shaped and including a plurality of rounded petals, the body being configured to transition from the collapsed condition to an expanded condition with a second lateral cross-section when a medical apparatus is passed through the lumen, the second lateral cross-section having a maximum dimension larger than a maximum dimension of the first lateral cross-section;
   inserting the medical apparatus through the lumen of the body such that the medical apparatus transitions the body from the collapsed condition to the expanded condition; and
   removing the medical apparatus from the lumen of the body, whereby the body returns from the expanded condition to the collapsed condition.

14. The method of claim 13, further comprising removing the medical apparatus through the lumen to allow the body to return to the collapsed condition.

15. The method of claim 13, wherein the insertion location is the ascending aorta.

16. The method of claim 13, wherein the insertion location is the left ventricle.

17. An introducer sheath, comprising:
   a body having a lumen extending between a leading end and a trailing end and having a collapsed condition with a first lateral cross-section, the first lateral cross-section being flower-shaped, the body being configured to transition from the collapsed condition to an expanded condition with a second lateral cross-section when an apparatus is passed through the lumen, the second lateral cross-section being substantially circular and having a maximum dimension larger than a maximum dimension of the first lateral cross-section,
   wherein the body is configured to have an intermediate condition in which one of the leading end and the trailing end has the first lateral cross-section and the other of the leading end and the trailing end has the second lateral cross-section.

* * * * *